United States Patent [19]

Yamahira et al.

[11] Patent Number: 4,514,386

[45] Date of Patent: Apr. 30, 1985

[54] CREAM PREPARATION

[75] Inventors: Yoshiya Yamahira, Osaka; Katsuhiko Shima, Kobe; Chikako Matsusaka, Osaka, all of Japan; Tetsuo Noguchi, Lawrence, Kans.

[73] Assignee: Sumitomo Chemical Company, Limited, Osaka, Japan

[21] Appl. No.: 558,571

[22] Filed: Dec. 6, 1983

Related U.S. Application Data

[63] Continuation of Ser. No. 366,703, Apr. 8, 1982, abandoned.

[30] Foreign Application Priority Data

Apr. 14, 1981 [JP] Japan .............................. 56-564494

[51] Int. Cl.³ ............................................ A01U 31/78
[52] U.S. Cl. ..................................................... 424/81
[58] Field of Search ........................................ 424/81

[56] References Cited

U.S. PATENT DOCUMENTS 4,123,433  2/1979  Sherlock .............................. 424/266
4,139,625  10/1978  Sherlock .............................. 424/266

OTHER PUBLICATIONS

Chem. Abst., 95-103322X (1981).

Primary Examiner—Stanley J. Friedman
Attorney, Agent, or Firm—Birch, Stewart, Kolasch & Birch

[57] ABSTRACT

An antiinflammatory cream preparation which comprises an antiinflammatory substance hardly soluble in water in a base composition at a concentration of 0.05 to 1.5% by weight based on the preparation, the base composition comprising a medium chain fatty acid triglyceride of which the fatty acid has 6 to 12 carbon atoms, carboxyvinyl polymer and purified water in a weight proportion of 1–25:0.3–3:75–99, and with an adjusted pH of 4 to 10. The cream preparation is excellent in the availability of the antiinflammatory substance contained therein and advantageously is low in stimulation and high in safety.

10 Claims, No Drawings

CREAM PREPARATION

This application is a continuation of application Ser. No. 366,703 filed Apr. 8, 1982, now abandoned.

The present invention relates to a cream preparation. More particularly, it relates to a cream preparation comprising a pharmacologically active substance which is hardly soluble in water.

For local application, a pharmacologically active substance which is hardly soluble in water is usually formulated in solution type preparation such as an ointment wherein the active substance is present in a state being dissolved in any appropriate non-aqueous (e.g. propyleneglycol, macrogol) or organic (e.g. ethanol, acetone) solvent so as to enhance its availability. However, a preparation which contains macrogol is sticky and/or stimulates the rectal mucosa. In the case of a preparation containing an organic solvent, its application directly to wound or mucosa is not favorable and its occlusive dressing technique can not be applied.

As a result of an extensive study, it has now been found that the use of a certain specific base composition affords a suspension type preparation which can show an excellent availability of an active ingredient contained therein as in a solution type preparation with favorable feeling on the use. The present invention is based on the above finding.

The cream preparation of the invention comprises a pharmacologically active substance which is hardly soluble in water in a base composition comprising a medium chain fatty acid triglyceride of which the fatty acid has from 6 to 12 carbon atoms, a carboxyvinyl polymer and purified water, and is adjusted to a pH of 4 to 10.

As the pharmacologically active substance usable in the cream preparation of the present invention, there may be included, for example steroidal and non-steroidal antiinflammatory substances such as fluorometholone, prednisolone, dexamethasone, triamcinolone, diflorazone diacetate, indomethacin, ibuprofen and flurubiprofen. The concentration of the active substance may be usually from 0.05 to 1.5% by weight based on the preparation.

The base composition in the cream preparation comprises medium chain fatty acid triglyceride of which the fatty acid has from 6 to 12 carbon atoms, carboxyvinyl polymer and purified water.

As the fatty acid triglyceride, there may be used caproic acid triglyceride, capric acid triglyceride, caprylic-capric acid triglyceride, etc.

The carboxyvinyl polymer is a hydrophilic polymer comprising acrylic acid as the major component. Specific examples are "Carbopol 934", "Carbopol 940", "Carbopol 941", etc. manufactured by Goodrich Co., Ltd.

For achievement of excellent feeling on its use, good dispersibility and high stability, the weight proportion of the medium chain fatty acid triglyceride, the carboxyvinyl polymer and the purified water is preferred to be 1-25:0.3-3:75-99. The pH of the cream preparation may be adjusted usually to a pH between 4 and 10 by the addition of a pH controlling agent such as water-soluble organic amines (e.g. diisopropanolamine).

If necessary, any other additive may be incorporated into the base composition or the preparation. Examples of such additive are a dispersing aid such as glycols (e.g. glycerol, propylene glycol) or sugar fatty acid esters, an absorbing aid such as diisopropyl adipate, etc.

A typical procedure for production of the cream preparation comprises dispersing the active substance in an aqueous solution of the carboxyvinyl polymer, adding a water-soluble organic amine thereto to make a gel and adding the medium chain fatty acid triglyceride to the gel for emulsification. Alternatively, the water-soluble organic amine may be incorporated after the addition of the medium chain fatty acid triglyceride.

The base of the cream preparation according to the present invention is low in stimulation and high in safety. Therefore, it can be applied not only to an ordinary skin but also to a mucosa such as rectum, eye and mouth, and its occlusive dressing technique which is generally executed in the field of dermatology is applicable.

The excellent availability of the active substance in the cream preparation of the invention may be understood from the results in the following Experiment 1 which shows the transfer rate of indomethacin into muscle.

EXPERIMENT 1

The availability of indomethacin in the cream preparation obtained as in Example 1 was compared with that of a gel ointment comprising indomethacin in the same concentration as in the said cream preparation ("Inteban ointment" manufactured by Sumitomo Chemical Co., Ltd.) and that of an absorptive ointment (Japanese Pharmacopoeia) comprising indomethacin in the same concentration as in the said cream preparation.

Namely, 100 mg of the preparation to be tested were applied onto the hair-cut abdomen part of a rat within a circle of 3 cm in diameter. After 6 hours, the rat was sacrificed, and the amount of indomethacin in the muscle inside the medicated part was quantitatively determined.

The results are shown in the following table:

TABLE 1

| Preparation | Type | Concentration of indomethacin in muscle ($\mu$g/g) |
| --- | --- | --- |
| Example 1 | Suspension | 1.11 ± 0.28 |
| control (Gel ointment) | Solution | 1.05 ± 0.33 |
| Control (Absorptive ointment) | Suspension | 0.57 ± 0.15 |

Note:
Average of 4 animals ± SE.

Presently preferred embodiments of the invention are illustratively shown in the following Examples.

EXAMPLE 1

To a suspension of indomethacin (1 g) in glycerol (5 g), carboxyvinyl polymer ("Carbopol 940") (1 g) and purified water (92.6 g) were added thereto, following by stirring for swelling. Then, isopropanolamine (0.4 g) was added thereto for gellation. The resultant mixture was admixed with medium chain fatty acid triglyceride ("ODO" manufactured by Nisshin Oil Mfg. Co., ltd.) (3 g) for emulsification to give a cream preparation comprising indomethacin.

EXAMPLE 2

To a mixture of fluorometholone (0.05 g) and carboxyvinyl polymer ("Carbopol 940") (0.5 g), purified water (83.8 g) was added, followed by stirring for swelling. Diisopropanolamine (0.4 g) was added thereto for gellation. The resultant mixture was admixed with medium chain fatty acid triglyceride ("Migriol 810" manufactured by Dynamit Novel A.G.) (15 g) and sugar fatty acid ester ("DK ester F-160" manufactured by Daiichi Kogyo Seiyaku Co., Ltd.) (0.25 g) for emulsification to give a cream preparation comprising fluorometholone.

What is claimed is:

1. A cream preparation which consist essentially of a pharmacologically active antiinflammatory substance which is hardly soluble in water in a base composition comprising 1 to 25 parts by weight of a medium chain fatty acid triglyceride of which the fatty acid has 6 to 12 carbon atoms, 0.3 to 3 parts by weight of a carboxypolymethylene and 75 to 99 parts by weight of purified water with an adjusted pH of 4 to 10, based on the weight of the base composition.

2. The cream preparation according to claim 1, wherein the antiinflammatory substance is indomethacin.

3. The cream preparation according to claim 1, wherein the antiinflammatory substance is fluorometholone.

4. The cream preparation according to claim 1, wherein the active substance is included at a concentration of 0.05 to 1.5% by weight based on the preparation.

5. The cream preparation according to claim 1 wherein the medium chain fatty acid triglyceride is selected from the group consisting of caproic acid triglyceride, capric acid triglyceride, and caprylic-capric acid triglyceride.

6. The cream preparation according to claim 1 wherein the carboxypolymethylene is a hydrophilic polymer comprising acrylic acid as the major component thereof.

7. The cream preparation according to claim 1 wherein a dispersing aid or absorbing aid is incorporated into the base composition, said dispersing or absorbing aid being selected from the group consisting of glycerol, propylene glycol, sugar fatty acid esters and diisopropyl adipate.

8. The cream preparation according to claim 1 wherein the active antiinflammatory substance is selected from the group consisting of fluorometholone, prednisolone, dexamethasone, triamcinolone, diflorazone diacetate, indomethacin, ibuprofen and flurubiprofen.

9. The cream preparation according to claim 1 wherein the active antiinflammatory substance is present in an amount of about 0.05 to 1.15% by weight based on the weight of the cream preparation.

10. The cream preparation according to claim 1 wherein the pH is adjusted by the addition of a water-soluble amine.

* * * * *

UNITED STATES PATENT AND TRADEMARK OFFICE
CERTIFICATE OF CORRECTION

PATENT NO.  : 4,514,386
DATED       : April 30, 1985
INVENTOR(S) : Yoshiya YAMAHIRA et al It is certified that error appears in the above-identified patent and that said Letters Patent is hereby corrected as shown below:

IN THE HEADING OF THE PATENT:

In Section [30], change, 56-564494 to --56-56494--

Signed and Sealed this

Thirteenth Day of August 1985

[SEAL]

*Attest:*

DONALD J. QUIGG

*Attesting Officer*  *Acting Commissioner of Patents and Trademarks*